United States Patent
Moszner et al.

(10) Patent No.: US 9,522,100 B2
(45) Date of Patent: Dec. 20, 2016

(54) DENTAL RESTORATIVE MATERIALS BASED ON POLYMERIZABLE AZIDES AND ALKYNES

(71) Applicant: Ivoclar Vivadent AG, Schaan (LI)

(72) Inventors: Norbert Moszner, Mauren (LI); Peter Burtscher, Rankweil (AT); Ulrich S. Schubert, Jena (DE); Martin Hager, Jena (DE); Bobby Happ, Jena (DE); Benedict Sandmann, Jena (DE)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/569,894

(22) Filed: Dec. 15, 2014

(65) Prior Publication Data
US 2015/0164750 A1 Jun. 18, 2015

(30) Foreign Application Priority Data
Dec. 15, 2013 (EP) ..................... 13197311

(51) Int. Cl.
| | | |
|---|---|---|
| A61K 6/087 | (2006.01) |
| C08G 73/00 | (2006.01) |
| C08G 73/06 | (2006.01) |
| C07D 251/54 | (2006.01) |
| C07D 493/10 | (2006.01) |
| A61K 6/00 | (2006.01) |
| C08G 63/676 | (2006.01) |
| C08G 63/52 | (2006.01) |

(52) U.S. Cl.
CPC .............. *A61K 6/087* (2013.01); *A61K 6/0023* (2013.01); *C07D 251/54* (2013.01); *C07D 493/10* (2013.01); *C08G 63/52* (2013.01); *C08G 63/676* (2013.01); *C08G 73/00* (2013.01); *C08G 73/0605* (2013.01)

(58) Field of Classification Search
None
See application file for complete search history.

(56) References Cited

U.S. PATENT DOCUMENTS

| 3,262,990 A * | 7/1966 | Hurwitz | C07C 2/867 523/303 |
| 2007/0298006 A1* | 12/2007 | Tomalia | A01N 25/10 424/78.03 |
| 2014/0329929 A1* | 11/2014 | Moszner | A61K 6/0002 523/116 |
| 2015/0164750 A1* | 6/2015 | Moszner | A61K 6/087 523/115 |

FOREIGN PATENT DOCUMENTS

| CA | 2845885 A1 | 3/2013 |
| WO | 2006012569 A1 | 2/2006 |
| WO | 2013034777 A2 | 3/2013 |

OTHER PUBLICATIONS

U.S. Appl. No. 14/569,894 505133 EICSEARCH—Structure search, USPTO, Jan. 29, 2016.*
Lutz, F., et al., A classification and evaluation of composite resin systems, J. Prosthet. Dent., Oct. 1983, vol. 50, pp. 480-488.
Peutzfeldt, A., Resin composites in dentistry: the monomer systems, Eur. J. Oral Sci., 1997, vol. 105, pp. 97-116.
Nicolson, J., et al., The chemistry of modern dental filling materials, J. Chem. Ed., 1999, vol. 76, pp. 1497-1501.
Stansbury, J., Curing dental resins and composites by photopolymerization, J. Esthet. Dent., 2000, vol. 12, pp. 300-308.
Moszner, N., et al., New Polymer-Chemical Developments in Clinical Dental Polymer Materials: Enamel-Dentin Adhesives and Restorative Composites, J. Polym. Sci. Part A: Polym. Chem., 2012, vol. 50, pp. 4369-4402.
Schuler, M., et al., Gold(I)-Catalyzed Alkoxyhalogenation of β-Hydroxy-a,a-Difluoroynones, Angew. Chem. Int. Ed., 2008, vol. 47, pp. 7927-7930.
Newman, M., et al., Synthesis of 3-Methoxyphthalic Anhydride, J. Org. Chem. 1980, vol. 45, pp. 3523-3524.
Abu-Orabi, S., Reaction of Acetylenedicarboxaldehyde Bis (diethyl acetal) with Bis (azidomethyl) benzene, J. Chem Eng. Data 1986, vol. 31, pp. 379-380.
Viohl, J., et al., "The chemistry of dental filling plastics", Carl Hanser Verlag, Munich Vienna, 1986, 8 pages.

* cited by examiner

*Primary Examiner* — Peter A Salamon
(74) *Attorney, Agent, or Firm* — Ann M. Knab; Thad McMurray

(57) ABSTRACT

The invention relates to a dental restorative material on the basis of at least one compound of one of the Formulae

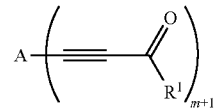

Formula I

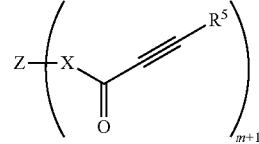

Formula I'

The invention also relates to the use of the dental restorative materials according to the invention for preparing dental composites, preferably composite blanks, which are suitable in particular for mechanical processing by means of computer-aided processing techniques such as milling and grinding processes, and which are suitable above all for preparing dental restoration materials such as inlays, onlays, crowns, bridges or veneering materials.

24 Claims, 6 Drawing Sheets

DENTAL RESTORATIVE MATERIALS BASED ON POLYMERIZABLE AZIDES AND ALKYNES

This application claims foreign priority benefits to European Patent Application EP 13197311.7 filed Dec. 15, 2013, which is hereby incorporated by reference.

The present invention relates to thermally-curing dental restorative materials, and in particular to dental composite materials with excellent mechanical properties for the preparation of dental composites for inlays, onlays, crowns, bridges or veneering materials.

Dental composites which e.g. are used as direct filling material, inlay, onlay, crowns or veneering material generally consist of a polymerizable organic matrix and of one or more fillers. Depending on the type of fillers, the monomer matrix and the application, the fill level can vary between approx. 50-90 wt.-%. According to the particle size and composition of the fillers, the composites are typically divided into macrofiller composites, homogeneous and heterogeneous microfiller composites, and hybrid composites (F. Lutz, R. W. Phillips, A classification and evaluation of composite resin systems, J. Prosthet. Dent. 50 (1983) 480-488).

The polymerizable organic matrix typically consists primarily of a mixture of monomers, initiator components, stabilizers and pigments (J. Viohl, K. Dermann, D. Quast, S. Venz, Die Chemie zahnärztlicher Füllungskunststoffe, Carl Hanser Verlag, Munich-Vienna 1986, 21-27). Mixtures of dimethacrylates are usually used as resins (cf. A. Peutzfeldt, Resin composites in dentistry: the monomer systems, Eur. J. Oral. Sci. 1997, 105, 97-116; J. W. Nicolson, H. M. Anstice, The chemistry of modern dental filling materials, J. Chem Ed. 1999, 76, 1497-1501; J. W. Stansbury, Curing dental resins and composites by photopolymerization, J. Esthet. Dent., 2000, 12, 300-308; N. Moszner, T. Hirt, New Polymer-Chemical Developments in Clinical Dental Polymer Materials: Enamel-Dentin Adhesives and Restorative Composites, J. Polym. Sci. Part A: Polym. Chem. 2012, 50, 4369-4402). Examples of this are the highly viscous dimethacrylates 2,2-bis[4-(2-hydroxy-3-methacryloyloxypropyl)-phenyl]propane (Bis-GMA) and 1,6-bis-[2-methacryloyloxyethoxycarbonylamino]-2,4,4-trimethylhexane (UDMA) and the less viscous dimethacrylates used as diluting monomers such as bismethacryloyloxymethyl-tricyclo[5.2.1]decane (TCDMA), decanediol-1,10-dimethacrylate ($D_3MA$) and triethylene glycol dimethacrylate (TEGDMA).

The known dimethacrylate-based dental composites can be cured by thermal, redox-initiated or light-induced radical polymerization using suitable initiators. However, it has proved to be a disadvantage of these composites that a polymer network in which filler particles are firmly integrated usually already forms within seconds and with a correspondingly low monomer conversion at the so-called gel point. Even at almost complete monomer conversion, the final 3-dimensional polymer network contains numerous unconverted double bonds. The cross-linking densities which can be attained with the known dimethacrylate-based dental composites, and thus also the mechanical properties which can be achieved, are therefore severely limited.

It is therefore an object of the invention to provide dental restorative materials which are characterized by higher conversion of the polyreactive groups, improved mechanical properties, and above all by an increased modulus of elasticity, and which are suitable in particular for preparing dental composites for inlays, onlays, crowns, bridges or veneering materials. Preferably, these dental restorative materials should be curable without metal catalyst and in a controlled manner without excessive generation of heat.

This object is achieved according to the invention by a dental restorative material which comprises at least one compound of Formula I or I'

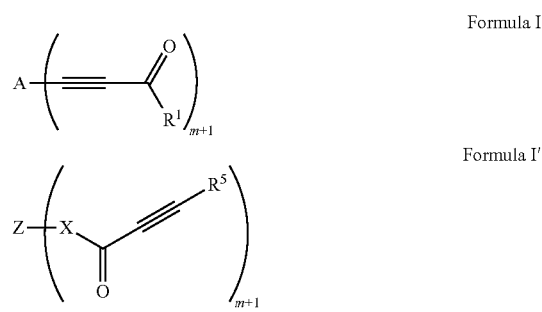

Formula I

Formula I' wherein

A represents in each case independently an (m+1)-valent phenylene radical, $R^1$ represents in each case independently an aliphatic linear or branched $C_1$-$C_{20}$ alkyl radical which can be interrupted by —O— or —S—, a phenyl radical which can carry one or more substituents that are preferably selected independently of each other from the group consisting of $CH_3$, $C_2H_5$, OH and $OCH_3$, or $R^3$, $R^2$ represents in each case independently H, an aliphatic linear or branched $C_1$-$C_{20}$ alkyl radical which can be interrupted by —O— or —S—, or a phenyl radical which can carry one or more substituents that are preferably selected independently of each other from the group consisting of $CH_3$, $C_2H_5$, OH and $OCH_3$, $R^3$ represents in each case independently —Z—Y—$R^2$ or —Z—C(=O)—≡—A($R^4$)$_m$, $R^4$ represents in each case independently —≡—C(=O)—$R^3$, $R^5$ represents in each case independently phenyl or $R^6$, $R^6$ represents in each case independently —C(=O)—X—$R^2$ or —C(=O)—X—Z($R^7$)m, $R^7$ represents in each case independently —X—C(=O)—≡—$R^6$, X represents in each case independently O, S, NH or $CH_2$, wherein X is missing when $R^5$ represents phenyl, Y represents in each case independently —C(O)—O—, —O—C(O)—, O or S, Z represents an (m+1)-valent aliphatic linear or branched $C_1$-$C_{20}$ alkylene radical which can be interrupted by —O— or —S—, or a phenylene radical which can carry one or more substituents that are preferably selected independently of each other from the group consisting of $CH_3$, $C_2H_5$, OH and $OCH_3$, and m in each case independently can assume the values 1 to 5.

The indication that a radical can be interrupted by a group, such as for example —O—, is to be understood such that the group is inserted into the carbon chain of the radical, i.e. is bordered on both sides by carbon atoms. The number of these groups is therefore smaller than the number of carbon atoms by at least 1 and the groups cannot be terminal. According to the invention, radicals which are not interrupted by the indicated groups are preferred.

According to the invention, only those compounds which are compatible with the chemical valence theory are considered.

Those compounds of Formulae I and I' are particularly preferred in which in each case independently of each other
A represents in each case independently an (m+1)-valent phenylene radical,
$R^1$ represents in each case independently an aliphatic linear or branched $C_1$-$C_{10}$ alkyl radical, in particular $C_1$-$C_6$ alkyl radical and preferably $C_1$-$C_3$ alkyl radical, which can be interrupted by —O— or —S—, or $R^3$,
$R^2$ represents in each case independently H, an aliphatic linear or branched $C_1$-$C_{10}$ alkyl radical, in particular $C_1$-$C_6$ alkyl radical and preferably $C_1$-$C_3$ alkyl radical, which can be interrupted by —O— or —S—,
$R^3$ represents in each case independently —Z—Y—$R^2$ or —Z—C(=O)—≡—A($R^4$)$_m$,
$R^4$ represents in each case independently —≡—C(=O)—$R^3$,
$R^5$ represents in each case independently phenyl or $R^6$,
$R^6$ represents in each case independently —C(=O)—X—$R^2$ or —C(=O)—X—Z($R^7$)$_m$,
$R^7$ represents in each case independently —X—C(=O)—≡—$R^6$,
X represents in each case independently O, S, NH or $CH_2$, wherein X is missing when $R^5$ represents phenyl,
Y represents in each case independently —C(O)—O— or —O—C(O)—,
Z represents an (m+1)-valent aliphatic linear or branched $C_1$-$C_{10}$ alkylene radical, in particular $C_1$-$C_6$ alkylene radical and preferably $C_1$-$C_3$ alkylene radical, which can be interrupted by —O— or —S—, or a phenylene radical which can carry one or more substituents that are preferably selected independently of each other from the group consisting of $CH_3$, $C_2H_5$, OH and $OCH_3$, and
m in each case independently can assume the values 1, 2 or 3.

Compounds are particularly preferred in this context in which all variables have one of the above-defined meanings and in particular one of the preferred meanings.

Figure 1:
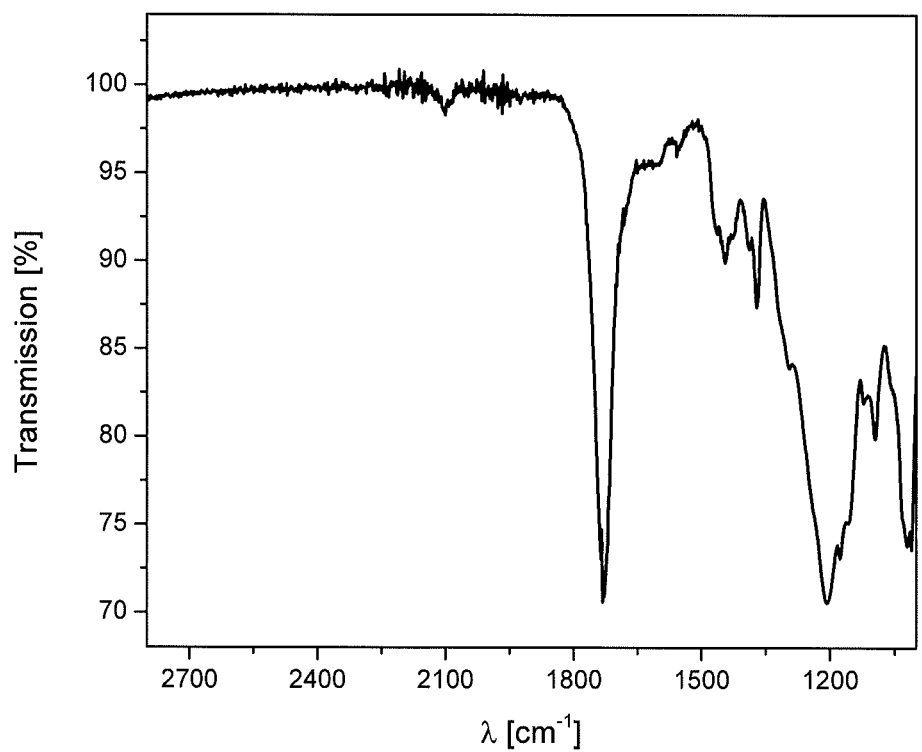
FIG. 1 shows the spectroscopy transmission of a monomer conversion via the decline in IR absorption of an azide group.

According to a preferred embodiment, the dental restorative material comprises at least one compound of one of Formulae IA to ID Formula IA

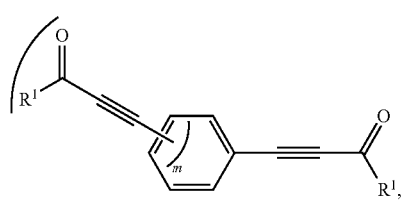

Formula IB

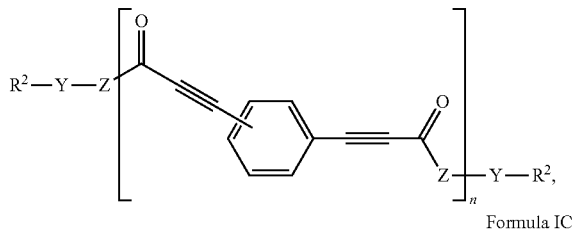

Formula IC

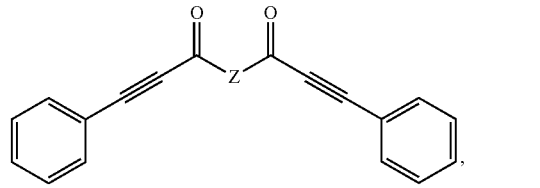

Formula ID

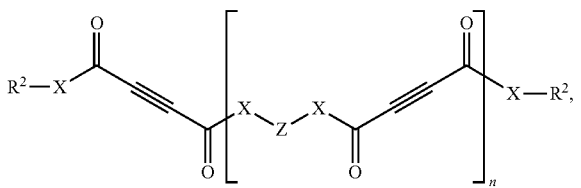

wherein
$R^1$ represents in each case independently an aliphatic linear or branched $C_1$-$C_{20}$ alkyl radical which can be interrupted by —O— or —S—, or a phenyl radical which can carry one or more substituents that are preferably selected independently of each other from the group consisting of $CH_3$, $C_2H_5$, OH and $OCH_3$,
$R^2$ represents in each case independently H, an aliphatic linear or branched $C_1$-$C_{20}$ alkyl radical which can be interrupted by —O— or —S—, or a phenyl radical which can carry one or more substituents that are preferably selected independently of each other from the group consisting of $CH_3$, $C_2H_5$, OH and $OCH_3$,
X represents in each case independently O, S, NH or $CH_2$,
Y represents in each case independently —C(O)—O—, —O—C(O)—, O or S,
Z represents an aliphatic linear or branched $C_1$-$C_{20}$ alkylene radical which can be interrupted by —O— or —S—, or a phenylene radical which can carry one or more substituents that are preferably selected independently of each other from the group consisting of $CH_3$, $C_2H_5$, OH and $OCH_3$,
m in each case independently can assume the values 1 to 5, and
n in each case independently can assume the values 2 to 10 and in particular the values 3 to 8.

Those compounds of Formulae IA to ID are particularly preferred in which in each case independently of each other
$R^1$ represents in each case independently an aliphatic linear or branched $C_1$-$C_{10}$ alkyl radical, in particular $C_1$-$C_6$ alkyl radical and preferably $C_1$-$C_3$ alkyl radical, which can be interrupted by —O— or —S—,
$R^2$ represents in each case independently H, an aliphatic linear or branched $C_1$-$C_{10}$ alkyl radical, in particular $C_1$-$C_6$ alkyl radical and preferably $C_1$-$C_3$ alkyl radical, which can be interrupted by —O— or —S—,
X represents in each case independently O, S, NH or $CH_2$, Y represents in each case independently —C(O)—O— or —O—C(O)—, Z represents an aliphatic linear or branched $C_1$-$C_{10}$ alkylene radical, in particular $C_1$-$C_6$ alkylene radical and preferably $C_1$-$C_3$ alkylene radical, which can be interrupted by —O— or —S—, or a phenylene radical which can carry one or more substituents that are preferably selected independently of each other from the group consisting of $CH_3$, $C_2H_5$, OH and $OCH_3$, m in each case independently can assume the values 1, 2 or 3, and n in each case independently can assume the values 3 to 8 and in particular the values 4 to 6.

Compounds are particularly preferred in this context in which all variables have one of the above-defined meanings and in particular one of the preferred meanings.

The dental restorative materials according to the invention typically comprise at least one multifunctional azide. Those dental restorative materials are preferred which comprise at least one azide of Formula II

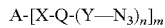

$$A\text{-}[X\text{-}Q\text{-}(Y\text{—}N_3)_n]_m \qquad \text{Formula II}$$

wherein

A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents, in particular selected from $C_1$-$C_5$ alkyl, OH, $OCH_3$ and $OCOCH_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents, in particular selected from $CH_3$, $C_2H_5$, $OCH_3$ and $OCOCH_3$, $R^3$ in each case independently represents H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4.

Those azides of Formula II are particularly preferred in which in each case independently of each other A represents —N= or an m-valent alkylene radical, cycloalkylene radical, heterocycloalkylene radical, arylene radical, heteroarylene radical, mixed alkylene-cyclyl radical such as alkylene-cyclyl radical, cyclyl-alkylene radical, cyclyl-alkylene-cyclyl radical or alkylene-cyclyl-alkylene-cyclyl-alkylene radical or cyclyl-O-cyclyl radical, wherein alkylene represents in each case independently a linear or branched aliphatic $C_1$-$C_{20}$ radical which can be interrupted by one or more —O—, —S—, —CO—O—, —O—CO— or —O—CO—O—, cycloalkylene represents in each case independently a cycloaliphatic $C_3$-$C_{12}$ radical, heterocycloalkylene represents in each case independently a heterocycloaliphatic $C_3$-$C_{12}$ radical, arylene represents in each case independently an aromatic $C_6$-$C_{12}$ radical, heteroarylene represents in each case independently a heteroaromatic $C_3$-$C_{12}$ radical, cyclyl represents in each case independently cycloalkylene, heterocycloalkylene, arylene or heteroarylene and the indicated radicals can in each case independently carry one or more substituents, in particular selected from $C_1$-$C_3$ alkyl, $OCH_3$ and $OCOCH_3$, Q in each case independently is missing or represents an (n+1)-valent linear or branched aliphatic $C_1$-$C_{10}$ alkylene radical which can be interrupted by one or more —O— or —S—, or a phenylene radical, wherein the indicated radicals in each case independently can carry one or more substituents, in particular selected from $CH_3$, $C_2H_5$, $OCH_3$ and $OCOCH_3$, $R^3$ in each case independently represents H or a $C_1$-$C_5$ alkyl radical and in particular a $C_1$-$C_3$ alkyl radical, X and Y in each case independently are missing or represent —O—, —S—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2, 3 or 4, n in each case independently can assume the values 1, 2 or 3 and in particular 1 or 2, and most preferably is 1.

Those compounds are particularly preferred in which all variables have one of the above-defined meanings and in particular one of the preferred meanings.

Moreover, dental restorative materials are preferred in which alkyne groups and azide groups are present entirely or approximately in stoichiometric ratio, and in particular in a ratio of 2:1-1:2, preferably in a ratio of 1.5:1-1:1.5, particularly preferably in a ratio of 1.1:1-1:1.1 and most preferably in a ratio of 1.05:1-1:1.05.

Those dental restorative materials are further preferred in which the compounds of Formula I or I', in particular of Formulae IA to ID, as well as the multifunctional azides have an average functionality of >2.2 and in particular >2.5. The average functionality refers to the average number of alkyne and azide groups, respectively, based on the molecules of compounds of Formula I or I', in particular of Formulae IA to ID, or the multifunctional azides contained in the dental restorative material.

It was surprisingly found that the dental restorative materials according to the invention, which comprise at least one alkyne of Formula I or I', in particular one of Formulae IA to ID, and at least one multifunctional azide, are excellently polymerizable and display a very high conversion of the polyreactive groups, and after curing have improved mechanical properties such as a much higher modulus of elasticity. Furthermore, these dental restorative materials can be cured without metal catalysts and exhibit a relatively low heat of reaction in the curing reaction. An uncontrollable progression of the reaction and in particular a thermal decomposition of the formed polyadducts is thus avoided.

Moreover, it has been shown that, based on the dental restorative materials according to the invention, polymer networks with customized properties can be prepared by suitable selection of the compounds of Formula I or I', in particular of Formulae IA to ID, and the multifunctional azides, in particular azides of Formula II, as well as by varying the average functionality of these compounds in the dental restorative material by setting a suitable mixture ratio in particular of the azides and alkynes. In this context, the network density increases with the average functionality of the compounds and the achieved conversion of the polymerizable groups. By varying the structure of the alkynes and/or azides, such as for instance the use of flexible or rigid spacers for bonding the azide and alkyne groups, respectively, the properties of the obtained polycycloaddition networks can be influenced further. Moreover, the degree of conversion of the functional groups and thus the cross-linking density can be further increased by thermal post-treatment. Finally, the mechanical properties can be further improved by adding fillers. The dental restorative materials according to the invention are therefore suitable in particular for preparing dental restoration materials such as high-modulus composite milling blanks for CAD/CAM-based processing techniques for preparing tooth-colored inlays, onlays, bridges or crowns.

Compounds of Formulae I and I' and in particular of Formulae IA to ID can be prepared easily according to synthesis methods known per se.

The lower molecular or oligomeric di- or higher functionalized alkynes of Formulae IA to ID can be easily prepared according to synthesis methods known per se.

The lower molecular di- or higher functionalized activated alkynes of Formulae IA can thus be obtained starting from di- or higher alkynylated benzene by ethynylation with suitable carboxylic acid esters:

Specific Example

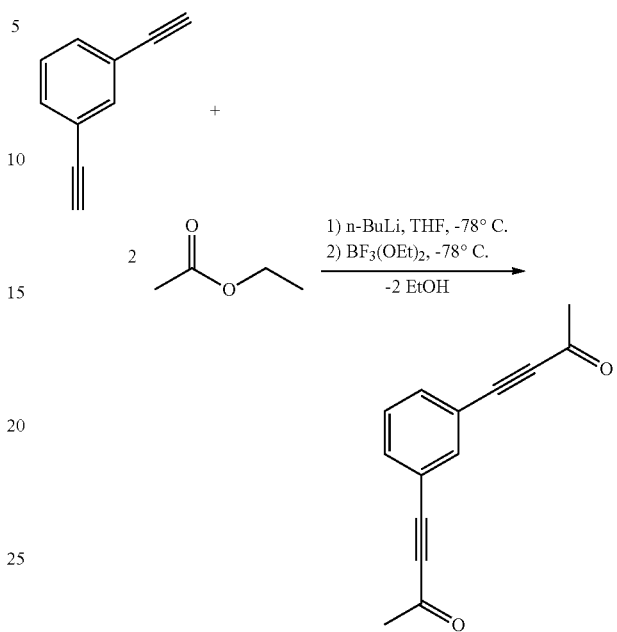

Analogously, the oligomeric alkynes of Formula IB can be obtained by ethynylation with suitable dicarboxylic acid esters.

Oligomeric higher functionalized activated alkynes of Formula ID can be obtained starting from acetylene dicarboxylates by reaction with compounds which are terminated with OH groups:

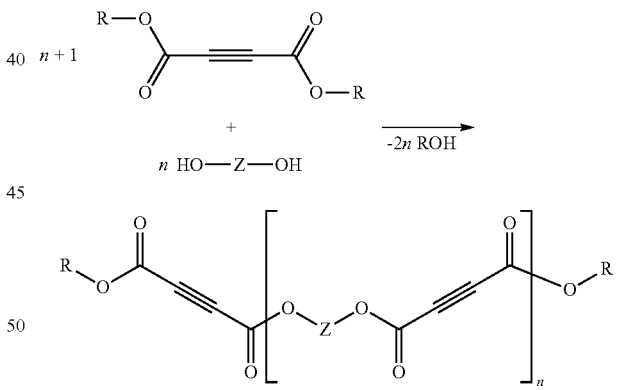

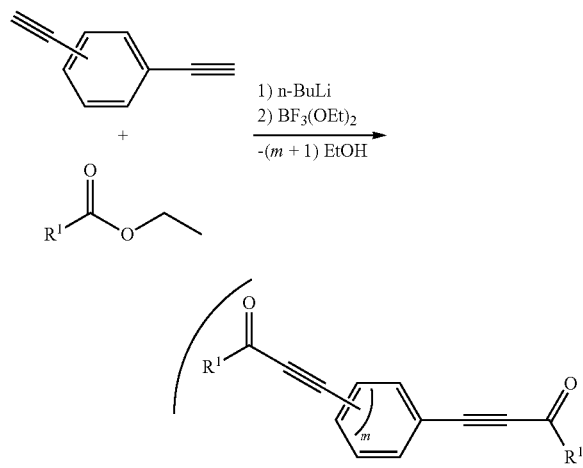

Specific Example

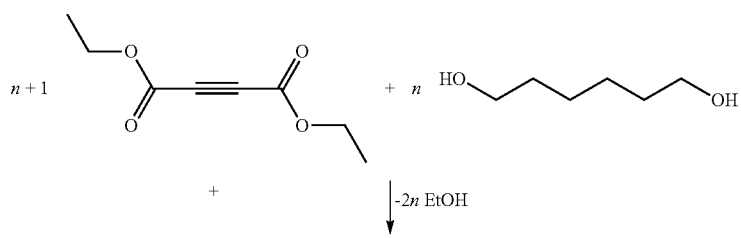

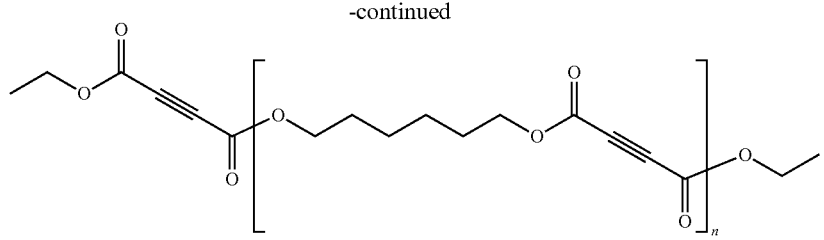
Examples of compounds of Formulae IA to ID according to the invention are:
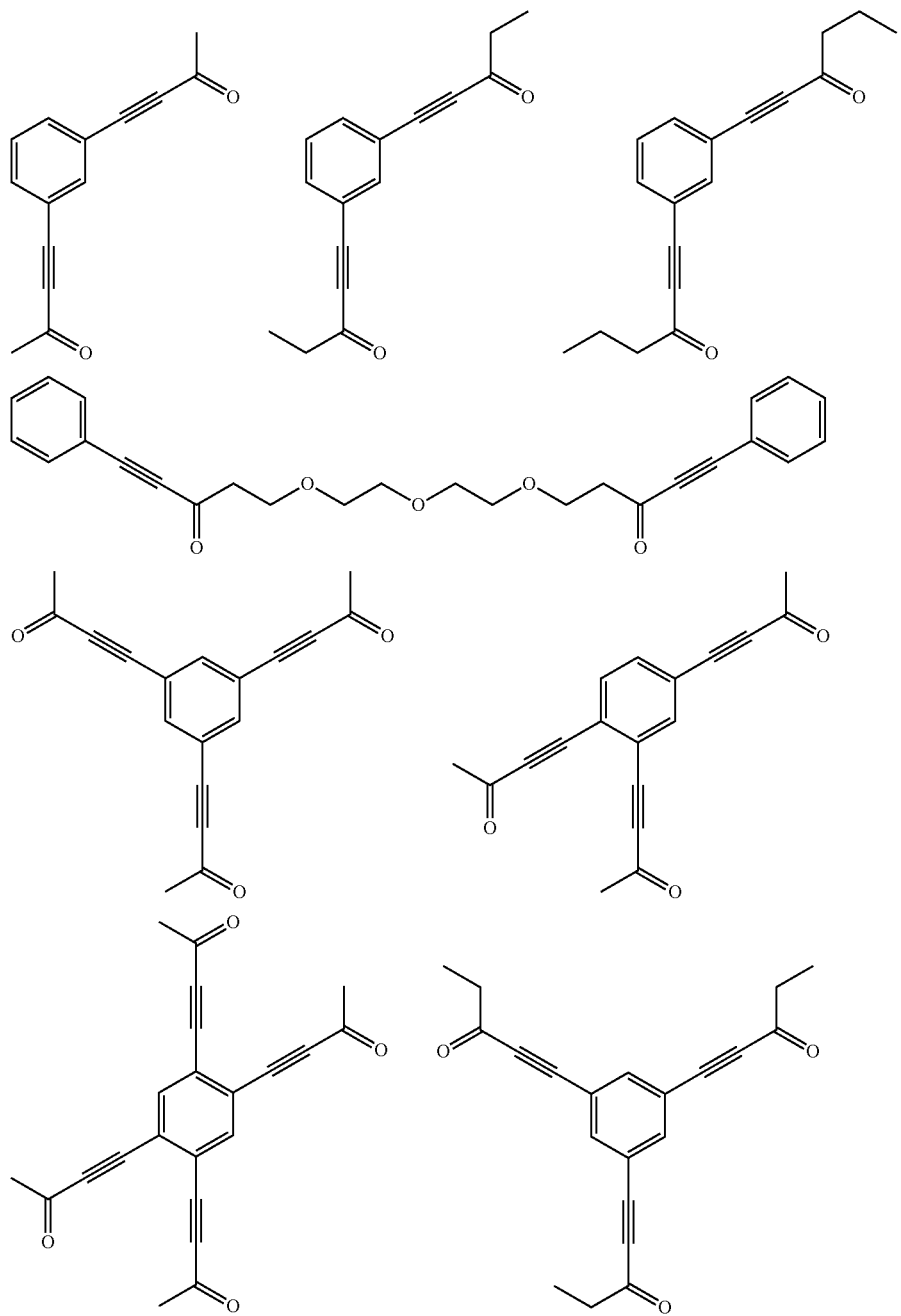

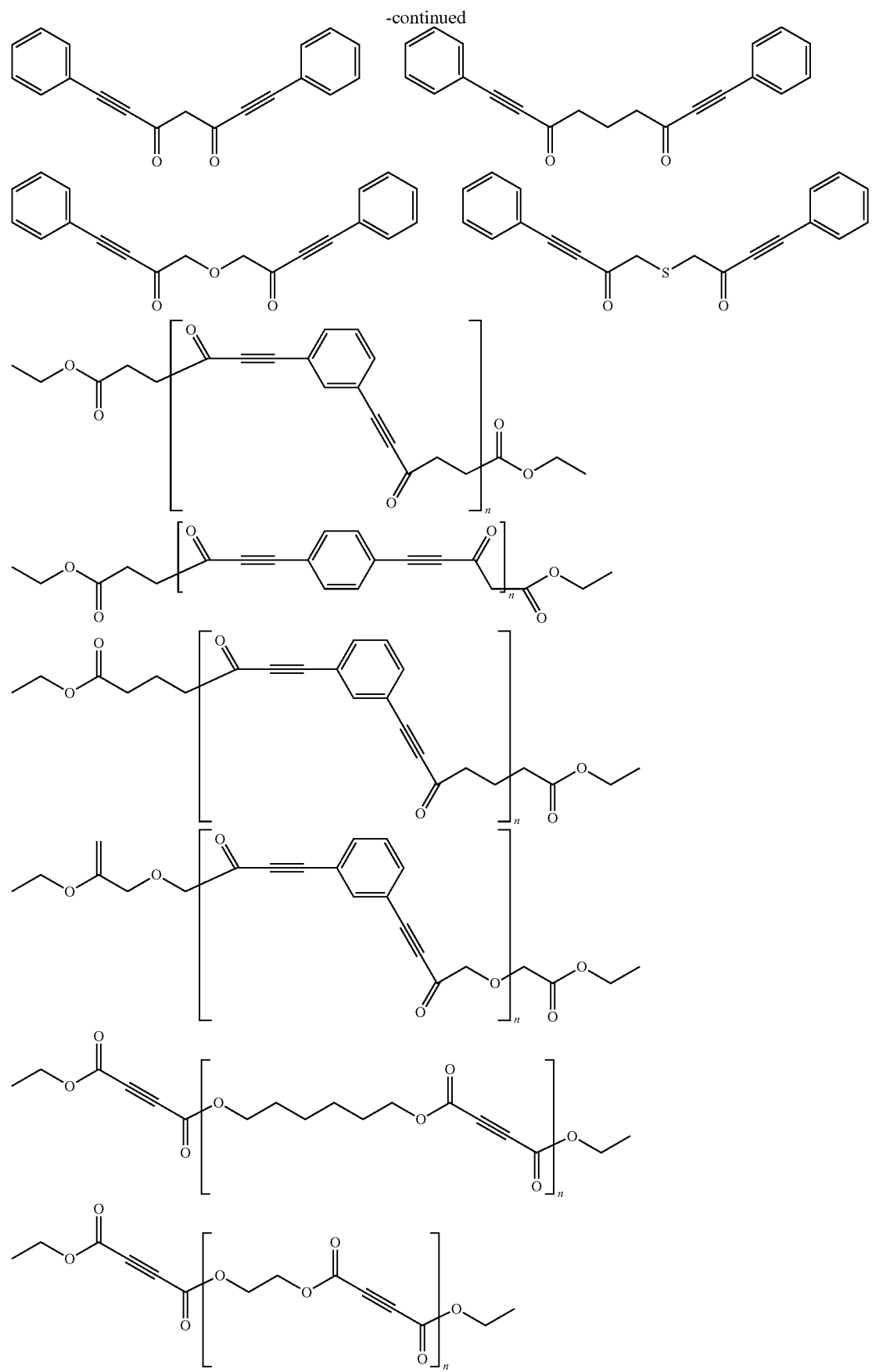

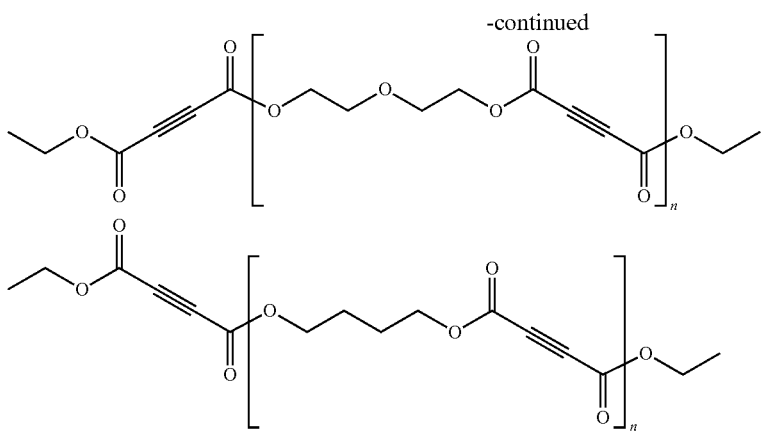

Compounds of Formula II are likewise easily available according to synthesis methods known per se. Azides of Formula II can thus, for example, be obtained by nucleophilic substitution of suitable di- or higher-functionalized halides (Z=Cl,Br,I) or p-toluenesulfonic acid esters (Z=OTos) with sodium azide $NaN_3$:

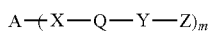
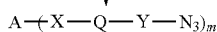

Specific Example

Reaction of 2,2,2-tri(chloromethyl)ethanol with sodium azide

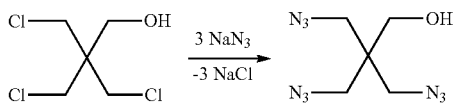

Furthermore, azide groups can be prepared in a manner known per se from aromatic hydrazines by diazotization, from alcohols by Mitsunobu reaction, or from isocyanates by addition of 2-azidoethanol.

Specific Example

Reaction of trimethyl hexamethylene diisocyanate with 2-azidoethanol or with 2-bromoethanol followed by sodium azide

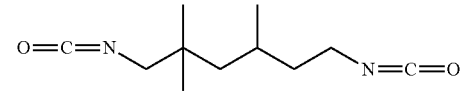

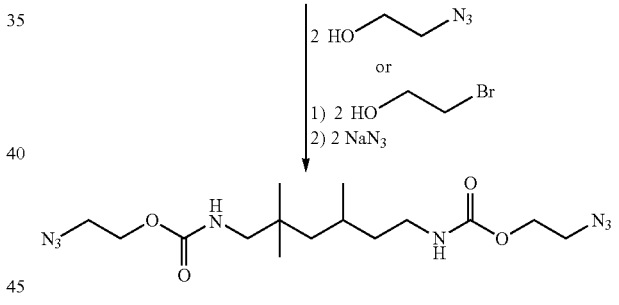

Examples of compounds of Formula II according to the invention are:

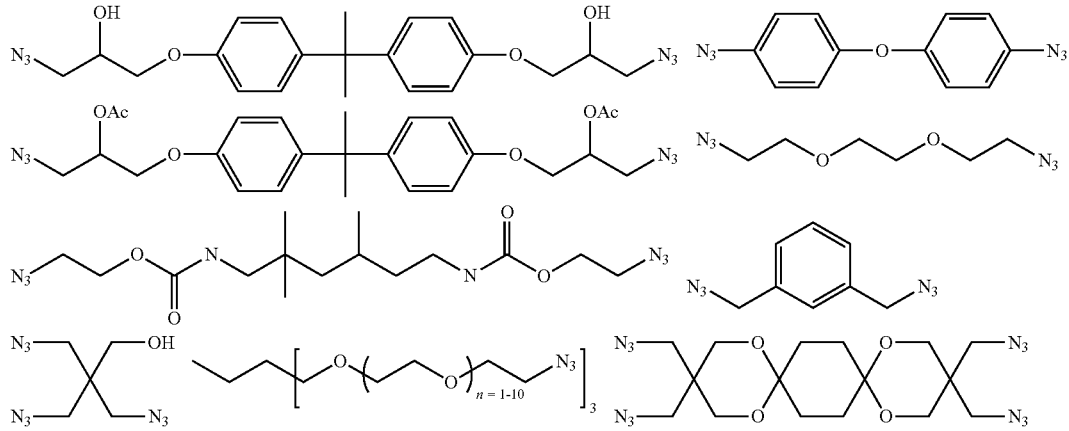

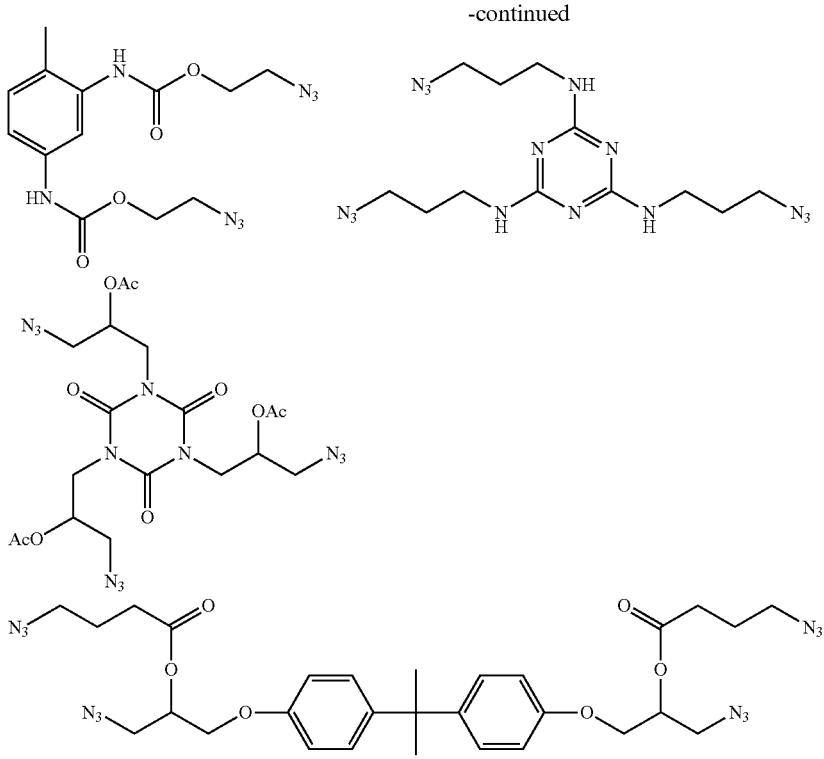

The dental restorative materials according to the invention preferably do not comprise a metal catalyst.

Hybrid materials which, in addition to at least one compound of Formula I or I', and in particular a compound of one of Formulae IA to ID, and at least one multifunctional azide, in particular at least one azide of Formula II, comprise radically polymerizable monomers can also be used according to the invention. Such hybrid materials can be cured in steps (first thermally- and then light-induced) or at the same time (light-induced).

In particular, mono- or polyfunctional (meth)acrylic acid derivatives are suitable as radically polymerizable monomers (co-monomers). By monofunctional (meth)acrylic acid derivatives are meant compounds with one (meth)acrylic acid group, by polyfunctional (meth)acrylic acid derivatives are meant compounds with two or more, preferably 2 to 4, (meth)acrylic acid groups. Polyfunctional monomers have a cross-linking effect.

Preferred mono- or polyfunctional (meth)acrylic acid derivatives are methyl-, ethyl-, hydroxyethyl-, butyl-, benzyl-, tetrahydrofurfuryl- or isobornyl(meth)acrylate, p-cumyl-phenoxyethylene glycol methacrylate (CMP-1E), bisphenol-A-di(meth)acrylate, Bis-GMA (an addition product of methacrylic acid and bisphenol-A-diglycidyl ether), ethoxylated or propoxylated bisphenol-A-dimethacrylate, such as e.g. the bisphenol-A-dimethacrylate SR-348c (Sartomer) with 3 ethoxy groups or 2,2-bis[4-(2-methacryloxy propoxy)phenyl]propane, UDMA (an addition product of 2-hydroxyethyl methacrylate (HEMA) and 2,2,4-trimethyl-hexamethylene diisocyanate), di-, tri- or tetraethylene glycol di(meth)acrylate, trimethylolpropane tri(meth)acrylate, pentaerythritol tetra(meth)acrylate, glycerol di- and tri-(meth) acrylate, 1,4-butanediol di(meth)acrylate, 1,10-decanediol di(meth)acrylate (D$_3$MA) and 1,12-dodecanediol di(meth) acrylate.

Particularly preferred mono- or polyfunctional (meth) acrylic acid derivatives are N-mono- or -disubstituted acrylamides, such as N-ethylacrylamide, N,N-dimethacrylamide, N-(2-hydroxyethyl)acrylamide or N-methyl-N-(2-hydroxyethyl)acrylamide, N-monosubstituted methacrylamides such as N-ethylmethacrylamide or N-(2-hydroxyethyl)methacrylamide as well as N-vinylpyrrolidone and allyl ether. These monomers are characterized by high hydrolysis stability and are particularly suitable as diluting monomers because of their relatively low viscosity.

Preferred polyfunctional (meth)acrylic acid derivatives with high hydrolysis stability are cross-linking pyrrolidones, such as 1,6-bis(3-vinyl-2-pyrrolidonyl)-hexane, bisacrylamides such as methylene or ethylene bisacrylamide and bis (meth)acrylamides such as N,N'-diethyl-1,3-bis(acrylamido)-propane, 1,3-bis(methacrylamido)-propane, 1,4-bis (acrylamido)-butane or 1,4-bis(acryloyl)-piperazine which can be synthesized by conversion from the corresponding diamines with (meth)acrylic acid chloride.

Preferably, mixtures of the above-mentioned monomers are used in this context.

Hybrid materials moreover preferably comprise an initiator for the radical polymerization.

Preferably, benzophenone, benzoin and their derivatives or α-diketones or their derivatives, such as 9,10-phenanthrenequinone, 1-phenyl-propane-1,2-dione, diacetyl or 4,4'-dichlorobenzil are used to initiate radical photopolymerization. Camphorquinone and 2,2-dimethoxy-2-phenyl-acetophenone are particularly preferably used, and quite particularly preferably α-diketones combined with amines, such as 4-(dimethylamino)-benzoate, N,N-dimethylamino-ethyl methacrylate, N,N-dimethyl-sym.-xylidine or triethanolamine as reductants. Norrish type I photoinitiators, in particular acyl or bisacylphosphine oxides, monoacyltri-alkyl- or diacyldialkylgermanium compounds, such as benzoyltrimethylgermanium, dibenzoyldiethylgermanium or bis-(4-methoxybenzoyl)diethylgermanium are also particularly suitable. Mixtures of the different photoinitiators can also be used, such as for example dibenzoyldiethylgermanium combined with camphorquinone and 4-dimethylaminobenzoic acid ethyl ester.

Preferably, redox-initiator combinations, such as for example combinations of benzoyl peroxide with N,N-dimethyl-sym.-xylidine or N,N-dimethyl-p-toluidine, are used as initiators for a polymerization carried out at room temperature. Furthermore, redox systems consisting of peroxides and reductants such as e.g. ascorbic acid, barbiturates or sulphinic acids, are also particularly suitable.

According to a preferred embodiment, the dental restorative materials according to the invention comprise no radically polymerizable monomers and no initiators for the radical polymerization.

The dental restorative materials according to the invention furthermore preferably also comprise organic or inorganic filler particles to improve the mechanical properties or to adjust the viscosity.

Preferred inorganic particulate fillers are amorphous spherical materials based on oxides, such as $ZrO_2$ and $TiO_2$, or mixed oxides of $SiO_2$, $ZrO_2$ and/or $TiO_2$ having an average particle size of from 0.005 to 2 µm, preferably 0.1 to 1 µm, nanoparticulate or microfine fillers such as pyrogenic silica or precipitated silica having an average particle size of from 5 to 200 nm, preferably 10 to 100 nm, minifillers such as quartz, glass ceramic or glass powders, for example from barium or strontium aluminium silicate glasses, having an average particle size of from 0.01 to 15 µm, preferably 0.1 to 1 µm, as well as radiopaque fillers such as ytterbium trifluoride or nanoparticulate tantalum(V) oxide or barium sulphate or mixed oxides of $SiO_2$ with ytterbium(III) oxide or tantalum(V) oxide having an average particle size of from 10 to 1000 nm, preferably 100 to 300 nm. The average particle size can in particular be determined by transmission or scanning electron microscopy or by laser diffraction. Preferably, transmission electron microscopy can be used in the range of from 1 nm to 50 nm, scanning electron microscopy can be used in the range of from 50 nm to 1 µm, and laser diffraction can be used in the range of from 1 µm to 100 µm to determine the average particle size. Fibrous fillers, nanofibres or whiskers are also suitable. To improve the bonding between the filler particles and the polycycloaddition matrix, in particular fillers based on $SiO_2$ can be surface modified with silanes that carry azide or alkyne groups, in particular activated alkyne groups. Examples of such silanes are 3-azidopropyltriethoxysilane and 4-[3-(triethoxysilyl)propoxy]-phenyl-but-3-in-2-one.

Moreover, the dental restorative materials according to the invention can comprise further additives, in particular stabilizers, flavorings, colorants, microbiocidal active ingredients, fluoride ion-releasing additives, optical brighteners, plasticizers, UV absorbers or solvents such as water or ethanol or corresponding solvent mixtures.

Particularly preferred are dental restorative materials based on at least one compound of Formula I or I', in particular at least one compound of one of Formulae IA to ID, and at least one multifunctional azide, in particular an azide of Formula II, which comprise the following components:
a) 0.1 to 70 wt.-%, in particular 1 to 60 wt.-%, preferably 5 to 50 wt.-% and particularly preferably 10 to 40 wt.-% of at least one compound of Formula I or I', in particular at least one compound of one of Formulae IA to ID,
b) 0.1 to 70 wt.-%, in particular 1 to 60 wt.-%, preferably 5 to 50 wt.-% and particularly preferably 10 to 40 wt.-% of at least one multifunctional azide, in particular at least one azide of Formula II,
c) 0 to 90 wt.-%, preferably 10 to 80 wt.-% and particularly preferably 20 to 70 wt.-% filler and
d) 0 to 70 wt.-%, preferably 1 to 50 wt.-% and particularly preferably 5 to 20 wt.-% solvent.

The invention also relates to the use of the dental restorative materials according to the invention for preparing dental composites, preferably composite blanks, which are suitable in particular for mechanical processing by means of computer-aided processing techniques such as milling and grinding processes, and which are suitable above all for preparing dental restoration materials such as inlays, onlays, crowns, bridges or veneering materials.

Furthermore, the invention also relates to the use of at least one compound of Formula I or I', in particular at least one compound of one of Formulae IA to ID, and at least one multifunctional azide, in particular at least one multifunctional azide of Formula II, as described above for preparing a dental restorative material and in particular a dental composite material.

The invention is explained in more detail below by means of nonlimiting examples.

EXAMPLES

Example 1

Synthesis of 4,4'-(1,3-phenylen)-bis-(but-3-in-2-one)

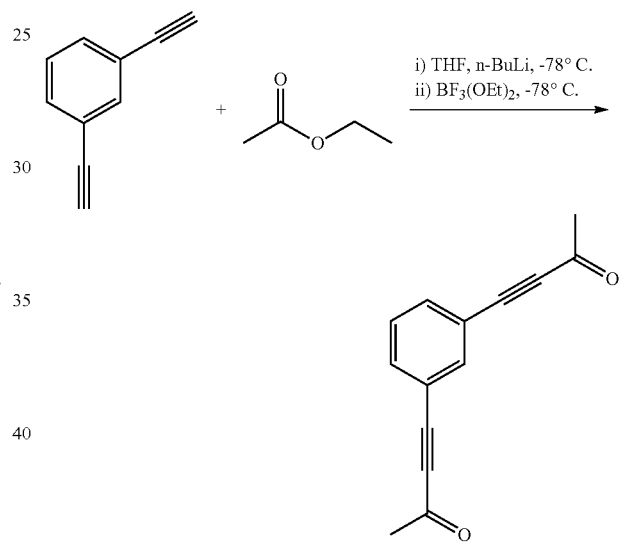

Synthesis was effected in analogy to M. Schuler et al., Angew. Chem. Int. Ed. 2008, 47, 7927-7930 (Supporting Information). 1,3-Diethynylbenzene (2.65 g, 21 mmol) was dissolved in dried THF (30 ml) und cooled to −78° C. Then, n-butyllithium (1.6 M in n-hexane, 30 ml, 48 mmol) was added dropwise under a nitrogen atmosphere followed by stirring for 30 min. Subsequently, a solution of ethylacetate (4.8 ml, 48 mmol), THF (30 ml) und boron trifluoride diethyl etherate (6.7 ml, 55 mmol) was slowly added. After 30 min the reaction mixture had a saturated $NH_4Cl$ solution added to it and was brought to room temperature. The organic phase was separated and the aqueous phase was further washed twice with ethylacetate (50 ml). After drying over anhydrous $Na_2SO_4$ the solution was concentrated and the product was isolated after twofold purification by column chromatography over silica (1. $CH_2Cl_2$, 2. hexane:ethylacetate (1:1)). 240 mg (5% yield) of the product was obtained as an orange colored solid.

$^1$H-NMR (300 MHz, $CDCl_3$): δ=7.76 (m, 1H), 7.63 (dd, J=7.8 Hz, J=1.6 Hz, 2H), 7.43 (t, J=7.8 Hz, 1H), 2.46 (s, 6H, $CH_3$).

$^{13}$C-NMR (75 MHz, $CDCl_3$): δ=184.1, 136.9, 134.6, 129.1, 120.8, 88.7, 87.8, 32.7.

Example 2

Synthesis of Oligoester 1

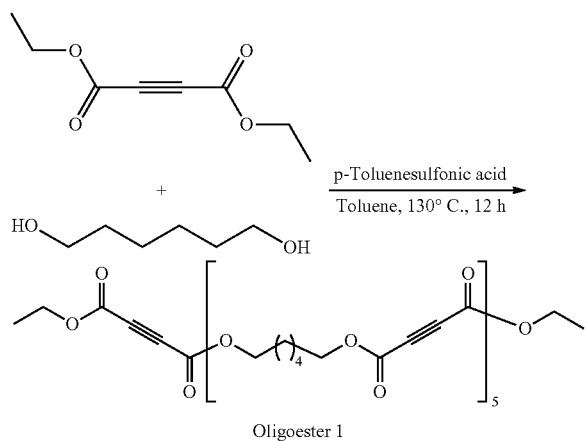

Oligoester 1

Diethyl acetylenedicarboxylate was obtained according to M. S. Newman et al., J. Org. Chem. 1980, 45, 3523-3524. Diethyl acetylene dicarboxylate (4.675 g, 27.5 mmol), 1,6-hexanediol (2.66 g, 22.5 mmol) and p-toluenesulfonic acid (300 mg, 1.75 mmol) were dissolved in toluene (50 ml) in a single-neck flask and heated at 130° C. for 12 h using a water trap. The reaction solution was washed three times with aqueous $NaHCO_3$ solution and the product was subsequently separated using preparative size exclusion chromatography (Bio-Beads S-X8, Eluent: $CH_2Cl_2$). 2.1 g (48% yield) of the product was obtained as a yellow oil.

$^1$H-NMR (300 MHz, $CDCl_3$): 4.27 (q, J=7.1 Hz, 4H, C(O)O—$CH_2$—$CH_3$), 4.21 (t, J=6.6 Hz, 4H, C(O)O—$CH_2$—$(CH_2)_4$—$CH_2$—), 1.67 (m, 4H, C(O)O—$CH_2$—$CH_2$—$(CH_2)_2$—$CH_2$—), 1.39 (m, 4H, C(O)O—$CH_2$—$CH_2$—$(CH_2)_2$—), 1.31 (t, J=7.1 Hz, 6H, $CH_3$).

$^{13}$C-NMR (75 MHz, $CDCl_3$): 151.8, 74.7, 74.6, 74.5, 66.7, 63.0, 28.0, 25.2, 13.8.

$M_n$ ($^1$H-NMR)=1150 g/mol (n=5); average content of triple bonds ($^1$H-NMR)=6; $M_n$ (SEC, PEG calibration)=1800 g/mol, $M_w$ (SEC, PEG calibration)=8500 g/mol.

Example 3

Figure 2:
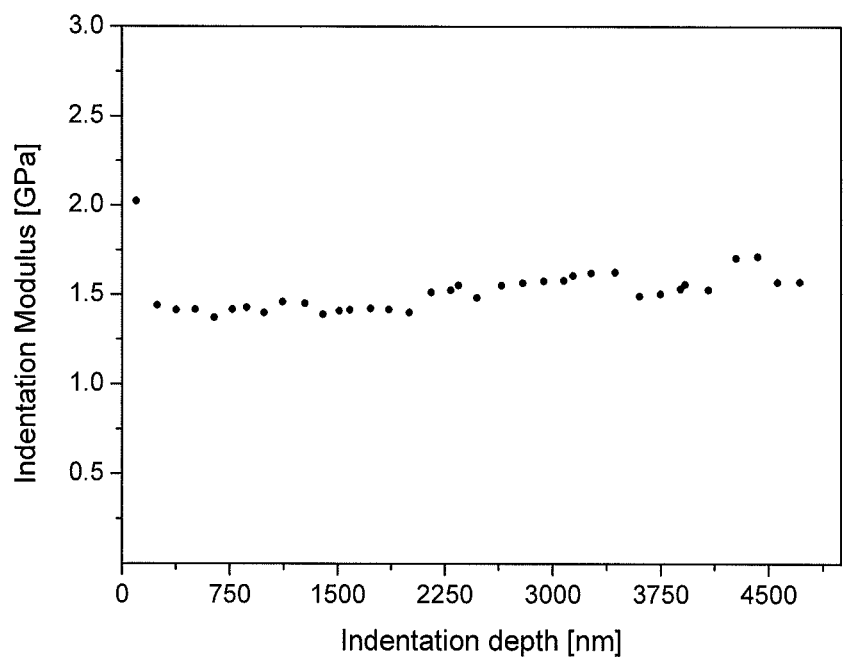
FIG. 2 shows the indentation modulus versus an indentation depth of polymers in accordance with the invention.

Synthesis of Polymer 1 by Azide-Alkyne Polycycloaddition Using an Activated Alkyne Oligoester 1 from Example 2 (200 mg) was dissolved in 1,3-bis-(azidomethyl)-benzene (80 mg, 0.43 mmol, prepared according to S. T. Abu-Orabi, J. Chem. Eng. Data 1986, 31, 379-380) and the solution was placed into a Teflon press sleeve (hight 0.5-1.0 mm, internal diameter 15 mm). It was then polymerized at 100° C. for 24 h on a glass slide. Yellow-red polymer 1 was obtained. The monomer conversion was tracked by means of ATR-IR spectroscopy via the decline in IR absorption of the azide group at 2100 $cm^{-1}$. The spectrum after 24 h is reproduced in FIG. 1 and indicates a monomer conversion of more than 95%. Then the modulus of elasticity of polyadduct 1 was determined by means of nanoindentation. This is a high local resolution method for the mechanical characterization of solids which is based on the measurement of load and displacement during the elastic-plastic contact of a hard test piece (diamond indenter having a radius of 4.7 μm) with the sample. The result is shown in FIG. 2. The value of the modulus of elasticity determined by means of nanoindentation was 1.5±0.2 GPa.

Figure 3:
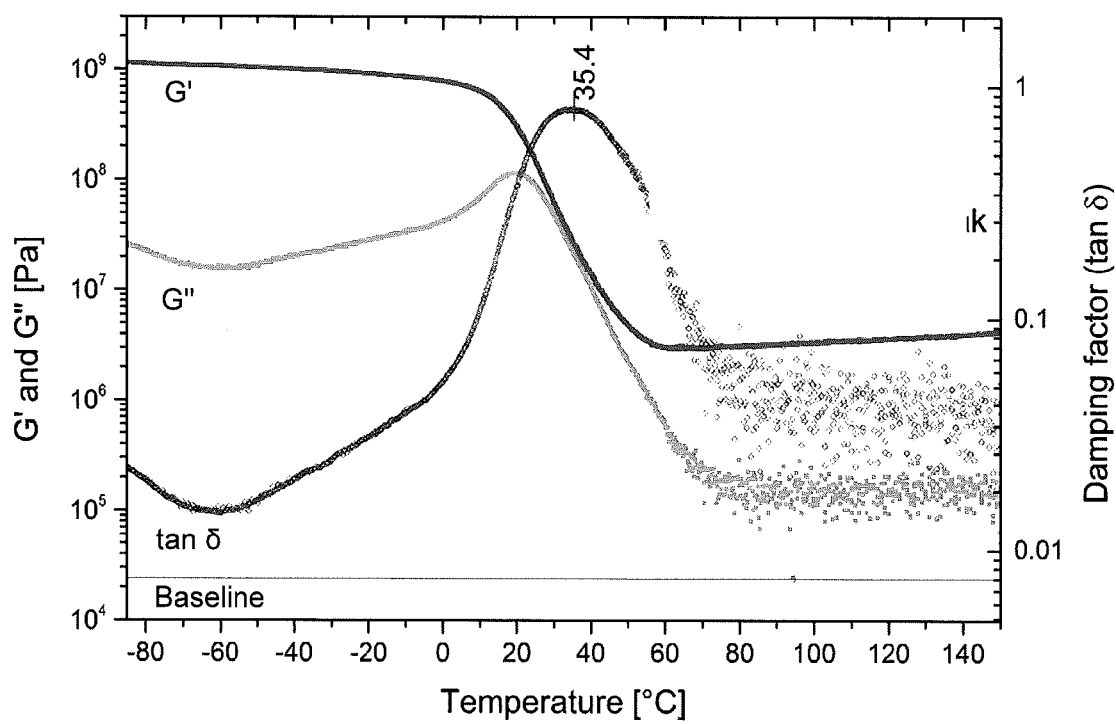
FIG. 3 shows a DMTA measurement of polymers in accordance with the invention.

For determining the glass transition temperature (Tg), a rod-shaped test piece of the polymers 1 was prepared and subsequently measured by means of dynamic-mechanical thermoanalysis (DMTA measurement on the rheometer Anton Paar MCR301). The result of the DMTA measurement is reproduced in FIG. 3. The glass transition temperature, which ensues from the local maximum of the loss angle function (tan δ function), was 35° C.

Figure 4:
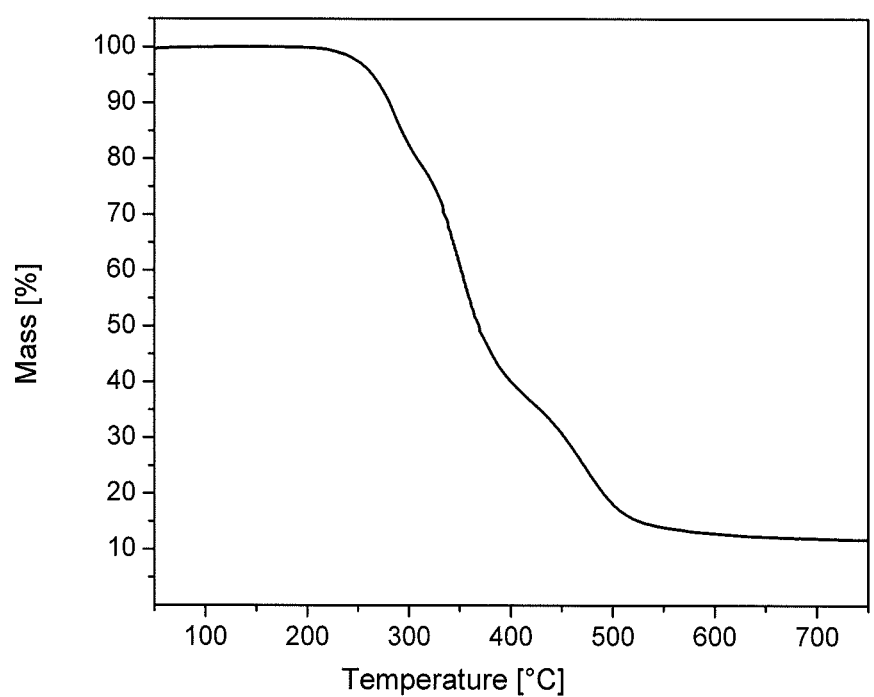
FIG. 4 shows a thermogravimetic analysis graph of polymers in accordance with the invention.

The thermal stability of polymer 1 was examined by way of thermogravimetric analysis (TGA; Netzsch TG 209 F1 Iris). All measurements were carried out under a nitrogen stream (20 ml/min) and in a temperature range between 20-800° C. (heating rate: 20 K/min). The result is shown in FIG. 4. Polymer 1 was shown to be stable up to a temperature of about 260° C.

Example 4

Heat Generation of Azide-Alkyne Polycycloadditions with Non-Activated and Activated Alkynes Equimolar binary mixtures of the monomers listed in the following Table 1 were prepared and their azid-alkyne polycycloaddition was tracked by means of differential scanning calorimetry (DSC). The differential scanning calorimetry (DSC) was performed on a Netzsch DSC 204 F1 Phoenix instrument under a nitrogen atmosphere. At least 10 mg of monomer mixture were weighted into an aluminum

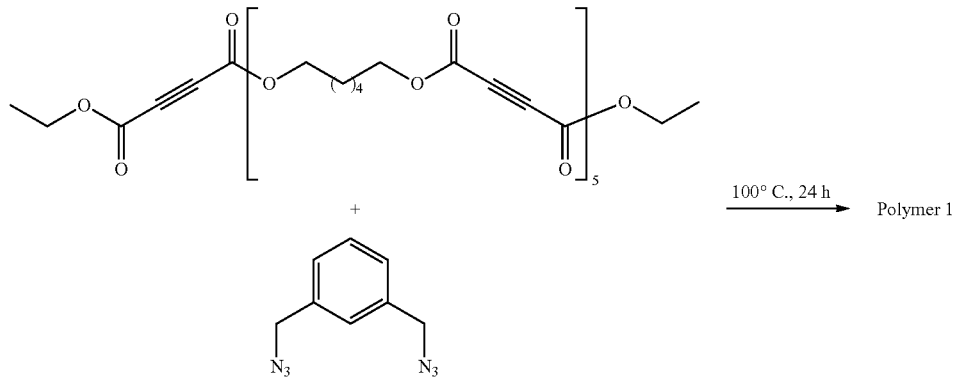

crucible and the crucibles were subsequently sealed. All measurements were carried out in a temperature range of −20 to 250° C. and at a heating rate of 10 K min⁻¹. The enthalpy values thus obtained are compiled in Table 1.

TABLE 1

| Polymer | Peak temperature (° C.) | Exothermal reaction enthalpy ΔH' (kJ · mol⁻¹) |
|---|---|---|
| Azide-alkyne cycloadditions with non-activated alkynes | | |
| M1-M2 (no copper) | 136 | −560 |
| M1-M2 (1.0 mol % CuOAc) | 80 | −404 |
| M1-M2 (2.0 mol % CuOAc) | 65 | −400 |
| Azide-alkyne cycloadditions with activated alkynes | | |
| M1-Oligoester 1 | 74 | −278 |
| M3-M4 (Example 1) | 129 | −284 |

A comparison of the results shows that mixtures with activated alkynes are characterized by a significantly lower heat generation.

Example 5

Synthesis of a Composite Via Azide-Alkyne Polycycloaddition with an Activated Alkyne

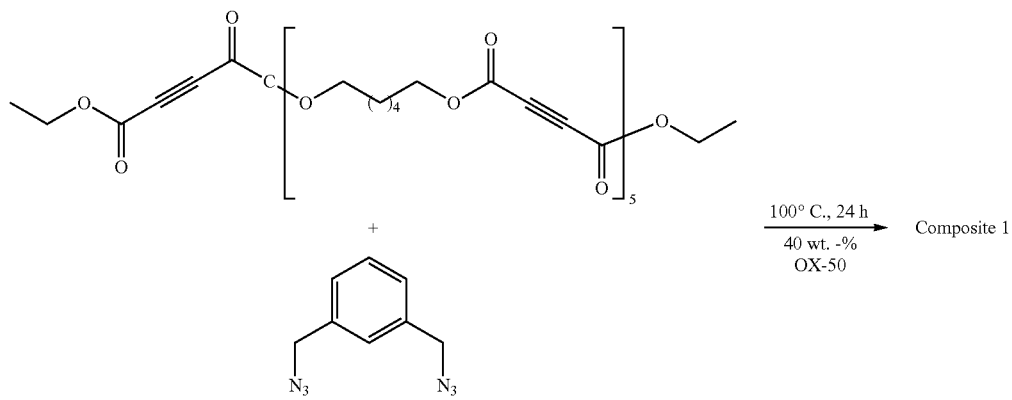

Figure 5:
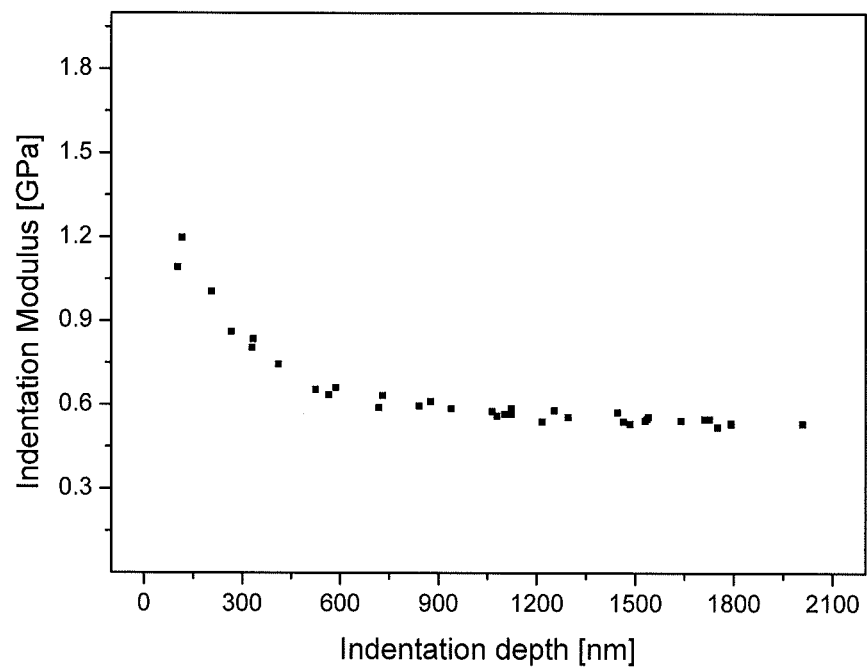
FIG. 5 shows the indentation modulus versus an indentation depth of polymers in accordance with the invention.
Figure 6:
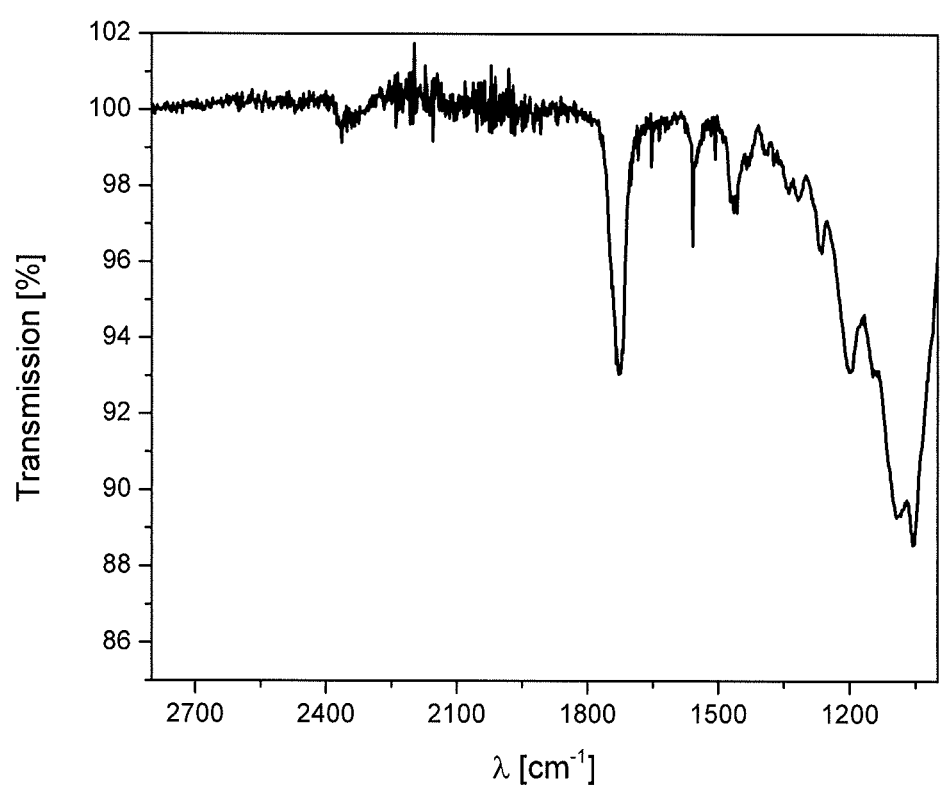
FIG. 6 shows the spectroscopy transmission of a monomer conversion via the decline in IR absorption of an azide group.

Oligoester 1 from Example 2 (200 mg) was dissolved in 1,3-diazido-methylbenzene (80 mg, 0.43 mmol). The filler OX-50 (185 mg) was subsequently added to the solution and mixed with a spatula until a homogenous mass had formed. The reaction mixture was then polymerized at 100° C. for 24 h on a glass slide. A light yellow polymer having an indentation modulus of 2.4±0.2 GPa (FIG. 5) and a monomer conversion >90% (FIG. 6) was obtained.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. Dental restorative material which comprises at least one compound of Formula I or I'

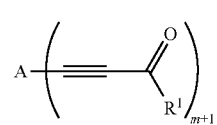

Formula I

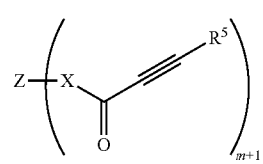

Formula I' wherein

A represents in each case independently an (m+1)-valent phenylene radical, $R^1$ represents in each case independently an aliphatic linear or branched $C_1$-$C_{20}$ alkyl radical which can be interrupted by —O— or —S—, a phenyl radical which can carry one or more substituents that are selected independently of each other from the group consisting of $CH_3$, $C_2H_5$, OH and $OCH_3$, or $R^3$, $R^2$ represents in each case independently H, an aliphatic linear or branched $C_1$-$C_{20}$ alkyl radical which can be interrupted by —O— or —S—, or a phenyl radical which can carry one or more substituents that are selected independently of each other from the group consisting of $CH_3$, $C_2H_5$, OH and $OCH_3$, $R^3$ represents in each case independently —Z—Y—$R^2$ or —Z—C(=O)—≡—A($R^4$)$_m$, $R^4$ represents in each case independently —≡—C (=O)—$R^3$, $R^5$ represents in each case independently phenyl or $R^6$, $R^6$ represents in each case independently —C(=O)— X—$R^2$ or —C(=O)—X—Z($R^7$)m, $R^7$ represents in each case independently —X—C (=O)—≡—$R^6$, X represents in each case independently O, S, NH or $CH_2$, wherein X is missing when $R^5$ represents phenyl, Y represents in each case independently —C(O)—O—, —O—C(O)—, O or S, Z represents an (m+1)-valent aliphatic linear or branched $C_1$-$C_{20}$ alkylene radical which can be interrupted by —O— or —S—, or a phenylene radical which can carry one or more substituents that are preferably selected independently of each other from the group consisting of $CH_3$, $C_2H_5$, OH and $OCH_3$, and m in each case independently can assume the values 1 to 5.

2. Dental restorative material according to claim 1, wherein in the Formulae I and I' in each case independently of each other A represents in each case independently an (m+1)-valent phenylene radical, $R^1$ represents in each case independently an aliphatic linear or branched $C_1$-$C_{10}$ alkyl radical, which can be interrupted by —O— or —S—, or $R^3$, $R^2$ represents in each case independently H, an aliphatic linear or branched $C_1$-$C_{10}$ alkyl radical, which can be interrupted by —O— or —S—, $R^3$ represents in each case independently —Z—Y—$R^2$ or —Z—C(=O)—=—A($R^4$)$_m$, $R^4$ represents in each case independently —=—C (=O)—$R^3$, $R^5$ represents in each case independently phenyl or $R^6$, $R^6$ represents in each case independently —C(=O)—X—$R^2$ or —C(=O)—X—Z($R^7$)$_m$, $R^7$ represents in each case independently —X—C (=O)—=—$R^6$, X represents in each case independently O, S, NH or $CH_2$, wherein X is missing when $R^5$ represents phenyl, Y represents in each case independently —C(O)—O— or —O—C(O)—, Z represents an (m+1)-valent aliphatic linear or branched $C_1$-$C_{10}$ alkylene radical, which can be interrupted by —O— or —S—, or a phenylene radical which can carry one or more substituents that are preferably selected independently of each other from the group consisting of $CH_3$, $C_2H_5$, OH and $OCH_3$, and m in each case independently can assume the values 1, 2 or 3.

3. Dental restorative material according to claim 1, which comprises at least one compound of one of Formulae IA to ID

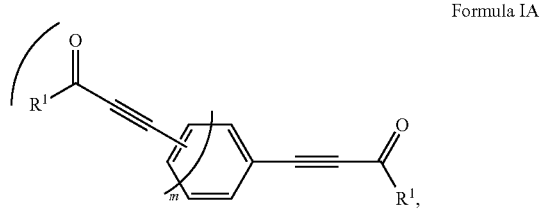

Formula IA

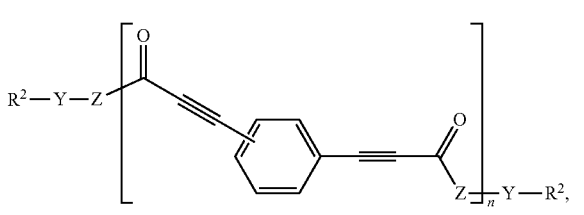

Formula IB

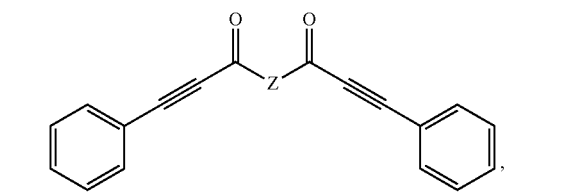

Formula IC

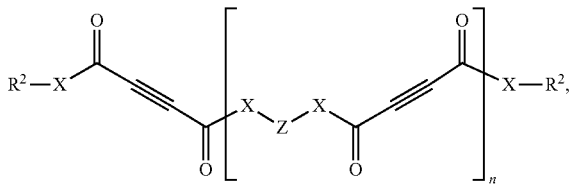

Formula ID wherein $R^1$ represents in each case independently an aliphatic linear or branched $C_1$-$C_{20}$ alkyl radical which can be interrupted by —O— or —S—, or a phenyl radical which can carry one or more substituents that are selected independently of each other from the group consisting of $CH_3$, $C_2H_5$, OH and $OCH_3$, $R^2$ represents in each case independently H, an aliphatic linear or branched $C_1$-$C_{20}$ alkyl radical which can be interrupted by —O— or —S—, or a phenyl radical which can carry one or more substituents that are selected independently of each other from the group consisting of $CH_3$, $C_2H_5$, OH and $OCH_3$, X represents in each case independently O, S, NH or $CH_2$, Y represents in each case independently —C(O)—O—, —O—C(O)—, O or S, Z represents an aliphatic linear or branched $C_1$-$C_{20}$ alkylene radical which can be interrupted by —O— or —S—, or a phenylene radical which can carry one or more substituents that are preferably selected independently of each other from the group consisting of $CH_3$, $C_2H_5$, OH and $OCH_3$, m in each case independently can assume the values 1 to 5, and n in each case independently can assume the values 2 to 10.

4. Dental restorative material according to claim 3, wherein in the Formulae IA to ID in each case independently of each other $R^1$ represents in each case independently an aliphatic linear or branched $C_1$-$C_{10}$ alkyl radical, which can be interrupted by —O— or —S—, $R^2$ represents in each case independently H, an aliphatic linear or branched $C_1$-$C_{10}$ alkyl radical, which can be interrupted by —O— or —S—, X represents in each case independently O, S, NH or $CH_2$, Y represents in each case independently —C(O)—O— or —O—C(O)—, Z represents an aliphatic linear or branched $C_1$-$C_{10}$ alkylene radical, which can be interrupted by —O— or —S—, or a phenylene radical which can carry one or more substituents that are preferably selected independently of each other from the group consisting of $CH_3$, $C_2H_5$, OH and $OCH_3$, m in each case independently can assume the values 1, 2 or 3, and n in each case independently can assume the values 3 to 8.

5. Dental restorative material according to claim 1, which further comprises at least one azide of Formula II A-[X-Q-(Y—$N_3$)$_n$]$_m$   Formula II wherein A represents —O—, —N=, —$NR^3$—, =N—N=, —$NR^3$—N=, =N—$NR^3$—, —$NR^3$—$NR^3$— or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{50}$ radical which can be interrupted by one or more —O—, —S—, —$NR^3$—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, cycloalkylene represents in each case independently a cycloaliphatic $C_3$-$C_{18}$ radical, heterocycloalkylene represents in each case independently a heterocycloaliphatic $C_3$-$C_{18}$ radical, arylene represents in each case independently an aromatic $C_6$-$C_{18}$ radical, heteroarylene represents in each case independently a heteroaromatic $C_3$-$C_{18}$ radical, cyclyl represents in each case independently cycloalkylene, heterocycloalkylene, arylene or heteroarylene and the indicated radicals in each case independently can carry one or more substituents selected from $C_1$-$C_5$ alkyl, OH, $OCH_3$ and $OCOCH_3$, Q in each case independently is missing or represents an (n+1)-valent linear or branched aliphatic $C_1$-$C_{20}$ alkylene radical which can be interrupted by one or more —O— or —S—, or a phenylene radical, wherein the indicated radicals in each case independently can carry one or more substituents selected from $CH_3$, $C_2H_5$, $OCH_3$ and $OCOCH_3$, $R^3$ in each case independently represents H or a $C_1$-$C_{10}$ alkyl radical, X and Y in each case independently are missing or represent —O—, —S—, —$NR^3$—, —CO—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2 to 6 and n in each case independently can assume the values 1 to 4.

6. Dental restorative material according to claim 5, wherein in Formula II in each case independently of each other A represents —N= or an m-valent alkylene radical, cycloalkylene radical, heterocycloalkylene radical, arylene radical, heteroarylene radical, mixed alkylene-cyclyl radical or cyclyl-O-cyclyl radical, wherein alkylene represents in each case independently a linear or branched aliphatic $C_1$-$C_{20}$ radical which can be interrupted by one or more —O—, —S—, —CO—O—, —O—CO— or —O—CO—O—, cycloalkylene represents in each case independently a cycloaliphatic $C_3$-$C_{12}$ radical, heterocycloalkylene represents in each case independently a heterocycloaliphatic $C_3$-$C_{12}$ radical, arylene represents in each case independently an aromatic $C_6$-$C_{12}$ radical, heteroarylene represents in each case independently a heteroaromatic $C_3$-$C_{12}$ radical, cyclyl represents in each case independently cycloalkylene, heterocycloalkylene, arylene or heteroarylene and the indicated radicals can in each case independently carry one or more substituents selected from $C_1$-$C_3$ alkyl, $OCH_3$ and $OCOCH_3$, Q in each case independently is missing or represents an (n+1)-valent linear or branched aliphatic $C_1$-$C_{10}$ alkylene radical which can be interrupted by one or more —O— or —S—, or a phenylene radical, wherein the indicated radicals in each case independently can carry one or more substituents selected from $CH_3$, $C_2H_5$, $OCH_3$ and $OCOCH_3$, $R^3$ in each case independently represents H or a $C_1$-$C_5$ alkyl radical or a $C_1$-$C_3$ alkyl radical, X and Y in each case independently are missing or represent —O—, —S—, —CO—O—, —O—CO—, —O—CO—O—, —CO—$NR^3$—, —$NR^3$—CO—, —O—CO—$NR^3$—, —$NR^3$—CO—O— or —$NR^3$—CO—$NR^3$—, m in each case independently can assume the values 2, 3 or 4, n in each case independently can assume the values 1, 2 or 3 and in particular 1 or 2, and most preferably is 1.

7. Dental restorative material according to claim 1, which comprises one or more radically polymerizable monomers.

8. Dental restorative material according to claim 7, which comprises methyl-, ethyl-, hydroxyethyl-, butyl-, benzyl-, tetrahydrofurfuryl- or isobornyl(meth)acrylate, p-cumyl-phenoxyethylene glycol methacrylate (CMP-1E), bisphenol-A-di(meth)acrylate, Bis-GMA, ethoxylated or propoxylated bisphenol-A-dimethacrylate, UDMA, di-, tri- or tetraethylene glycol di(meth)acrylate, trimethylolpropane tri(meth)acrylate, pentaerythritol tetra(meth)acrylate, glycerol di- or tri(meth)acrylate, 1,4-butanediol di(meth)acrylate, 1,10-decanediol di(meth)acrylate ($D_3MA$), 1,12-dodecanediol di(meth)acrylate, and/or one or more N-mono- or -disubstituted acrylamides, N-ethylacrylamide, N,N-dimethacrylamide, N-(2-hydroxyethyl)acrylamide, N-methyl-N-(2-hydroxyethyl) acrylamide, one or more N-monosubstituted methacrylamides, N-ethylmethacrylamide, N-(2-hydroxyethyl) methacrylamide, N-vinylpyrrolidone, one or more cross-linking allyl ethers, and/or one or more cross-linking pyrrolidones, 1,6-bis(3-vinyl-2-pyrrolidonyl)-hexane, one or more cross-linking bisacrylamides, methylene or ethylene bisacrylamide, one or more cross-linking bis(meth)acrylamides, N,N'-diethyl-1,3-bis(acrylamido)-propane, 1,3-bis(methacrylamido)-propane, 1,4-bis(acrylamido)-butane, 1,4-bis(acryloyl)-piperazine, or a mixture thereof.

9. Dental restorative material according to claim 1, which comprises organic and/or inorganic filler.

10. Dental restorative material according to claim 9, which comprises at least one inorganic particulate filler selected from the group consisting of amorphous spherical materials based on oxides or mixed oxides having an average particle size of from 0.005 to 2 μm, nanoparticulate or microfine fillers having an average particle size of from 5 to 200 nm, minifillers having an average particle size of from 0.01 to 15 μm, and radiopaque fillers having an average particle size of from 10 to 1000 nm.

11. Dental restorative material according to claim 1, which comprises a) 0.1 to 70 wt.-% of at least one compound of Formula I or I', b) 0.1 to 70 wt.-% of at least one multifunctional azide of Formula II, c) 0 to 90 wt.-% filler and d) 0 to 70 wt.-% solvent.

12. Method of using a dental restorative material according to claim 1 for preparing dental composites or dental restoration materials comprising inlays, onlays, crowns, bridges or veneering materials.

13. Method of using at least one compound of Formula I or I' as defined in claim 1, for preparing a dental restorative material comprising a dental composite material.

14. Dental restorative material according to claim 1, wherein in the Formulae I and I' in each case independently of each other
   $R^1$ represents in each case independently an aliphatic linear or branched $C_1$-$C_6$ alkyl radical, which can be interrupted by —O— or —S—, or $R^3$,
   $R^2$ represents in each case independently H, an aliphatic linear or branched $C_1$-$C_6$ alkyl radical, which can be interrupted by —O— or —S—, and
   Z represents an (m+1)-valent aliphatic linear or branched $C_1$-$C_6$ alkylene radical, which can be interrupted by —O— or —S—, or a phenylene radical which can carry one or more substituents that are preferably selected independently of each other from the group consisting of $CH_3$, $C_2H_5$, OH and $OCH_3$.

15. Dental restorative material according to claim 1, wherein in the Formulae I and I' in each case independently of each other
   $R^1$ represents in each case independently an aliphatic linear or branched $C_1$-$C_3$ alkyl radical, which can be interrupted by —O— or —S—, or $R^3$,
   $R^2$ represents in each case independently H, an aliphatic linear or branched $C_1$-$C_3$ alkyl radical, which can be interrupted by —O— or —S—, and
   Z represents an (m+1)-valent aliphatic linear or branched $C_1$-$C_3$ alkylene radical, which can be interrupted by —O— or —S—, or a phenylene radical which can carry one or more substituents that are preferably selected independently of each other from the group consisting of $CH_3$, $C_2H_5$, OH and $OCH_3$.

16. Dental restorative material according to claim 3, wherein in the Formulae IA to ID in each case independently of each other
   $R^1$ represents in each case independently an aliphatic linear or branched $C_1$-$C_6$ alkyl radical, which can be interrupted by —O— or —S—,
   $R^2$ represents in each case independently H, an aliphatic linear or branched $C_1$-$C_6$ alkyl radical, which can be interrupted by —O— or —S,
   Z represents an aliphatic linear or branched $C_1$-$C_6$ alkylene radical, which can be interrupted by —O— or —S—, or a phenylene radical which can carry one or more substituents that are selected independently of each other from the group consisting of $CH_3$, $C_2H_5$, OH and $OCH_3$, and
   n in each case independently can assume the values 4 to 6.

17. Dental restorative material according to claim 3, wherein in the Formulae IA to ID in each case independently of each other
   $R^1$ represents in each case independently an aliphatic linear or branched $C_1$-$C_3$ alkyl radical, which can be interrupted by —O— or —S—,
   $R^2$ represents in each case independently H, an aliphatic linear or branched $C_1$-$C_3$ alkyl radical, which can be interrupted by —O— or —S, and
   Z represents an aliphatic linear or branched $C_1$-$C_3$ alkylene radical, which can be interrupted by —O— or —S—, or a phenylene radical which can carry one or more substituents that are preferably selected independently of each other from the group consisting of $CH_3$, $C_2H_5$, OH and $OCH_3$.

18. Dental restorative material according to claim 9, which comprises at least one inorganic particulate filler selected from the group consisting of amorphous spherical materials based on oxides or mixed oxides having an average particle size of from 0.1 to 1 μm, nanoparticulate or microfine fillers having an average particle size of from 10 to 100 nm, minifillers having an average particle size of from 0.1 to 1 μm, and radiopaque fillers having an average particle size of from 100 to 300 nm.

19. Dental restorative material according to claim 1, which comprises
   a) 1 to 60 wt.-% of at least one compound of Formula I or I',
   b) 1 to 60 wt.-% of at least one multifunctional azide of Formula II,
   c) 10 to 80 wt.-% filler and
   d) 1 to 50 wt.-% solvent.

20. Dental restorative material according to claim 1, which comprises
   a) 5 to 50 wt.-% of at least one compound of Formula I or I',
   b) 5 to 50 wt.-% of at least one multifunctional azide of Formula II,
   c) 20 to 70 wt.-% filler and
   d) 5 to 20 wt.-% solvent.

21. Dental restorative material according to claim 1, which comprises
   a) 10 to 40 wt.-% of at least one compound of Formula I or I',
   b) 10 to 40 wt.-% of at least one multifunctional azide of Formula II,
   c) 0 to 90 wt.-% filler and
   d) 0 to 70 wt.-% solvent.

22. Dental restorative material according to claim 3, which comprises
   a) 0.1 to 70 wt.-% of at least one compound of Formulae IA to ID,
   b) 0.1 to 70 wt.-% of at least one multifunctional azide of Formula II,
   c) 0 to 90 wt.-% filler and
   d) 0 to 70 wt.-% solvent.

23. Method of using at least one compound of Formula IA to ID as defined in claim 3 for preparing a dental restorative material comprising a dental composite material.

24. Method of using at least one azide of Formula II as defined in claim 5 for preparing a dental restorative material comprising a dental composite material.

\* \* \* \* \*